US012629166B2

(12) United States Patent
Tada

(10) Patent No.: US 12,629,166 B2
(45) Date of Patent: May 19, 2026

(54) MEDICAL DEVICE

(71) Applicant: TERUMO KABUSHIKI KAISHA, Tokyo (JP)

(72) Inventor: Yuichi Tada, Santa Clara, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 902 days.

(21) Appl. No.: 17/860,017

(22) Filed: Jul. 7, 2022

(65) Prior Publication Data

US 2022/0346820 A1 Nov. 3, 2022

Related U.S. Application Data

(63) Continuation of application No. PCT/JP2020/014692, filed on Mar. 30, 2020.

(51) Int. Cl.
*A61B 17/32* (2006.01)
*A61B 17/00* (2006.01)
*A61B 17/3207* (2006.01)

(52) U.S. Cl.
CPC ............... *A61B 17/32002* (2013.01); *A61B 2017/00469* (2013.01); *A61B 2017/320741* (2013.01)

(58) Field of Classification Search
CPC ...... A61B 17/32002; A61B 17/320758; A61B 2017/22079; A61B 2217/007
See application file for complete search history.

(56) References Cited

U.S. PATENT DOCUMENTS

2013/0072951 A1* 3/2013 Trezza, II .......... A61B 10/0275
606/170
2014/0350485 A1* 11/2014 Sonderegger ....... B29C 45/1657
604/533

(Continued)

FOREIGN PATENT DOCUMENTS

JP 2012-170737 A 9/2012
JP 2018-110859 A 7/2018

(Continued)

OTHER PUBLICATIONS

English Translation of International Search Report dated Jun. 9, 2020, mailed in counterpart International Application No. PCT/JP2020/014692, 3 pages.

(Continued)

*Primary Examiner* — Bradley J Osinski
(74) *Attorney, Agent, or Firm* — Kim & Stewart LLP

(57) ABSTRACT

A medical device for removing an object in a body cavity includes a rotatable drive shaft having a lumen, a cutter at a distal portion of the shaft and by which the object is cut, a first rotation connection portion at a proximal portion of the shaft and by which a rotational force is transmitted to the shaft, a first fluid connection portion at the proximal portion and through which the object is removed with a fluid, and a handle including a second rotation connection portion connectable to the first rotation connection portion, a second fluid connection portion connectable to the first fluid connection portion, a rotation driving source connected to the second rotation connection portion and generating the rotational force, and a fluid driving source moving the fluid from the distal to proximal portions of the shaft via the first and second fluid connection portions.

20 Claims, 8 Drawing Sheets

(56)         References Cited

U.S. PATENT DOCUMENTS

| | | |
|---|---|---|
| 2017/0360466 A1 | 12/2017 | Brown et al. |
| 2018/0193052 A1 | 7/2018 | Govari et al. |
| 2019/0142452 A1 | 5/2019 | Trosper et al. |
| 2019/0223898 A1 | 7/2019 | Curtin et al. |
| 2021/0000498 A1 | 1/2021 | Shiraishi et al. |

FOREIGN PATENT DOCUMENTS

| | | |
|---|---|---|
| JP | 2019-521788 A | 8/2019 |
| WO | 2019/189078 A1 | 10/2019 |

OTHER PUBLICATIONS

English Translation of Written Opinion dated Jun. 9, 2020, mailed in counterpart International Application No. PCT/JP2020/014692, 5 pages.

* cited by examiner

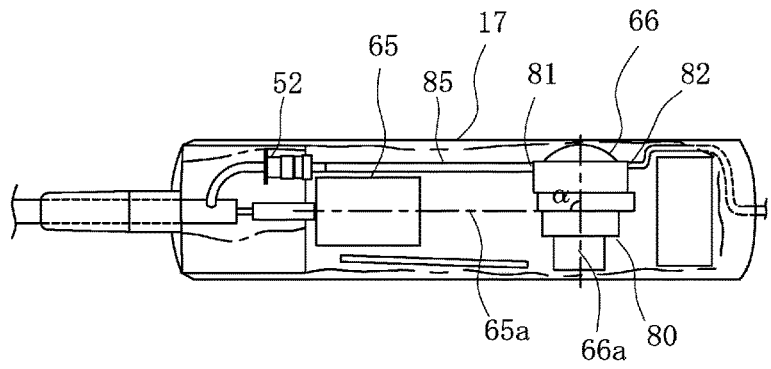
FIG. 8
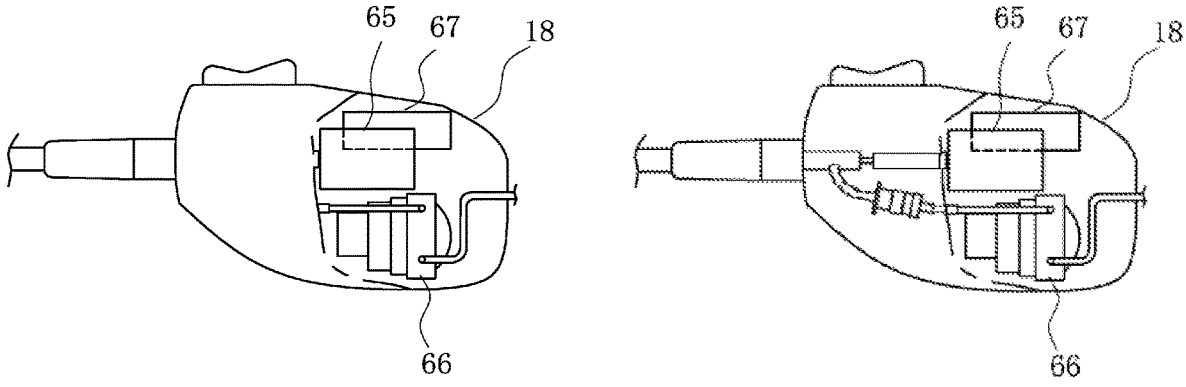
FIG. 9A                    FIG. 9B

MEDICAL DEVICE

CROSS-REFERENCE TO RELATED APPLICATION(S)

This application is a continuation of International Patent Application No. PCT/JP2020/014692 filed Mar. 30, 2020, the entire contents of which are incorporated herein by reference.

BACKGROUND OF THE INVENTION

Field of the Invention

This disclosure relates to a medical device for removing an object in a body cavity.

Background Art

Examples of a treatment method for a stenosed site caused by a plaque, a thrombus, and the like in a blood vessel include a method for dilating the blood vessel by using a balloon, and a method for causing a mesh-shaped or coil-shaped stent to indwell the blood vessel as a support for the blood vessel. However, it is difficult for these methods to treat a stenosed site that is hardened by calcification or a stenosed site that is formed at a bifurcated portion in the blood vessel. Thus, methods for cutting and removing a stenotic material such as a plaque or a thrombus have been developed and used.

A conventional medical device used for this treatment includes a cutting portion that cuts an object in a blood vessel by rotating. Such a medical device further includes a drive shaft to which the cutting portion is attached at a distal portion thereof and a lumen through which the cut object is aspirated. The drive shaft is connected to a rotation driving source such as a motor, and the lumen is connected to a fluid driving source such as a pump.

In such a medical device, a shaft portion including the drive shaft and the lumen, the rotation driving source, and the fluid driving source may be integrated.

In the medical device in which the shaft portion, the rotation driving source, and the fluid driving source are integrated, when any one of those components is damaged, all of the portions are required to be discarded. Thus, there has been a medical device in which the shaft portion and the rotation driving source or the fluid driving source are separate, but the fluid driving source is disposed in a console outside a handle. In such a case, the drive shaft of the shaft portion needs to be connected to the rotation driving source, and the lumen of the shaft portion needs to be connected to the fluid driving source at a position away from the handle portion. When the medical device is used, however, it takes time and effort for the operator to connect the drive shaft and the lumen to the rotation driving source and the fluid driving source, respectively. In addition, there are risks that the operator forgets to connect the lumen to the fluid driving source, or the connection is inadequate.

SUMMARY OF THE INVENTION

A medical device for removing an object in a body cavity, includes a rotatable drive shaft having a lumen, a cutter disposed at a distal portion of the drive shaft and by which the object is cut, a first rotation connection portion at a proximal portion of the drive shaft and by which a rotational force is transmitted to the drive shaft, a first fluid connection portion at the proximal portion of the drive shaft and through which the object that has been moved with a fluid through the lumen is removed, and a handle including: a second rotation connection portion connectable to the first rotation connection portion, a second fluid connection portion connectable to the first fluid connection portion, a rotation driving source connected to the second rotation connection portion and configured to generate the rotational force, and a fluid driving source configured to move the fluid from the distal portion to the proximal portion of the drive shaft via the first and second fluid connection portions.

In the medical device configured as described above, since the rotation connection portion of the drive shaft and the fluid connection portion of the drive shaft can be integrally attached to the handle, the lumen is reliably connected to the fluid driving source.

BRIEF DESCRIPTION OF THE DRAWINGS

FIG. 8 is an enlarged bottom view showing an internal structure of a handle portion.

FIGS. 9A and 9B are front views each showing an internal structure of a handle portion.

DESCRIPTION OF EMBODIMENTS

Figure 1:
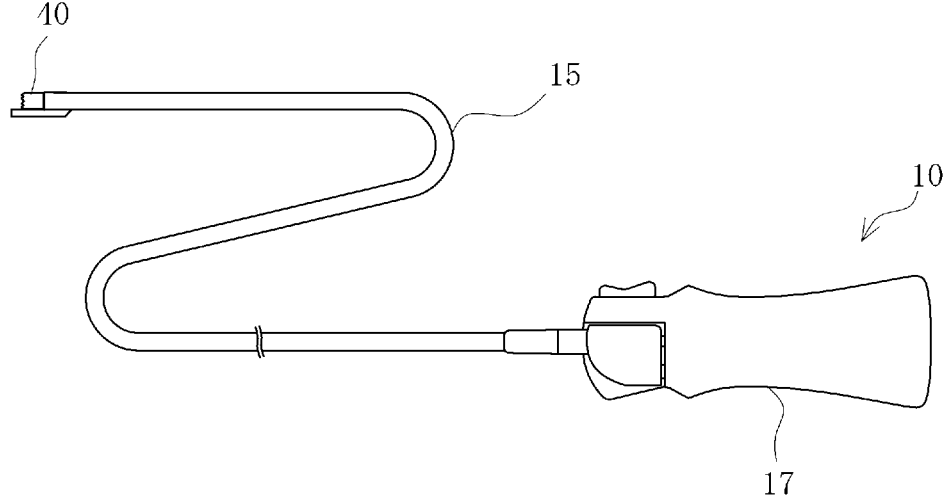
FIG. 1 is an overall front view showing a medical device.

Hereinafter, embodiments will be described with reference to the drawings. It is noted that dimensional ratios in the drawings are exaggerated for convenience of description and may differ from actual ratios. In the present specification, a side of a medical device 10 to be inserted into a body cavity is referred to as a "distal end" or a "distal side", and a side to be operated by an operator is referred to as a "proximal end" or a "proximal side".

A medical device 10 according to an embodiment is inserted into a blood vessel in an acute lower limb ischemia or a deep vein thrombosis, and is used for a procedure for destroying and removing a thrombus, a plaque, an atheroma, a calcified lesion, and the like. It is noted that an object to be removed is not necessarily limited to the thrombus, the plaque, the atheroma, and the calcified lesion, and any object that may be present in a body lumen or a body cavity can be removed by the medical device 10.

Figure 2:
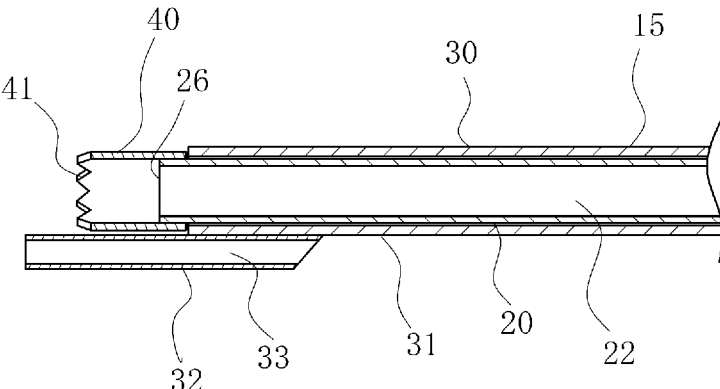
FIG. 2 is an enlarged cross-sectional view showing a distal portion of a medical device.

As shown in FIGS. 1 and 2, the medical device 10 includes a shaft portion 15 including a long drive shaft 20 that is rotationally driven, and an outer tube 30 that accommodates the drive shaft 20. A handle portion 17 is provided at a proximal portion of the shaft portion 15. A cutting portion 40 that cuts an object such as a thrombus is provided at a distal portion of the drive shaft 20.

The drive shaft 20 transmits a rotational force to the cutting portion 40. A lumen 22 for conveying the cut object to the proximal side is formed in the drive shaft 20. The drive shaft 20 penetrates the outer tube 30, and the cutting portion 40 is fixed to the distal portion thereof. The drive shaft 20 includes, at the distal end, an inlet portion 26 into which debris (e.g., cut thrombus or the like), that is, an object to be aspirated, enters.

The drive shaft 20 is flexible and capable of transmitting a rotational power applied from the proximal side to the distal side. The drive shaft 20 may be formed of one member as a whole, or may be formed of a plurality of members. The drive shaft 20 may have a spiral slit or groove formed by laser processing or the like in order to adjust rigidity along the rotational axis. In addition, the distal portion and a proximal portion of the drive shaft 20 may be formed of different members.

As a constituent material for the drive shaft 20, for example, stainless steel, a shape memory alloy such as a nickel-titanium alloy, an alloy made of silver, copper, zinc, and the like (e.g., silver brazing filler metal), an alloy made of gold, tin, and the like (e.g., solder component), a cemented carbide such as tungsten carbide, polyolefins such as polyethylene and polypropylene, polyamides, polyesters such as polyethylene terephthalate, fluoropolymers such as an ethylene tetrafluoroethylene copolymer (ETFE), polyether ether ketone (PEEK), and polyimides can be preferably used. In addition, the drive shaft 20 may be made of a plurality of materials, and a reinforcing member such as a wire rod may be embedded therein.

The outer tube 30 includes an outer tube main body 31 that rotatably accommodates the drive shaft 20, and a distal tube 32 that is fixed to a side surface of a distal portion of the outer tube main body 31.

The distal portion of the outer tube main body 31 is located on a proximal side of the cutting portion 40. By rotating the outer tube main body 31, the cutting portion 40 can be directed to an object to be removed. In addition, the outer tube main body 31 may include a curved portion bent at a predetermined angle at the distal portion thereof. By rotating the curved portion in the outer tube main body 31, the cutting portion 40 can easily connect to an object to be removed.

The distal tube 32 is fixed to an outer peripheral surface of the distal portion of the outer tube main body 31. The distal tube 32 has a guide wire lumen 33 into which a guide wire can be inserted. Therefore, the medical device 10 is a rapid exchange type device in which the guide wire lumen 33 is formed only at a distal portion thereof.

Constituent materials for the outer tube main body 31 and the distal tube 32 are not particularly limited, and for example, stainless steel, a shape memory alloy such as a nickel-titanium alloy, titanium, an alloy made of titanium, silver, copper, zinc, and the like (e.g., silver brazing filler metal), an alloy made of gold, tin, and the like (e.g., solder component), a cemented carbide such as tungsten carbide, polyolefins such as polyethylene and polypropylene, polyamides, polyesters such as polyethylene terephthalate, or various elastomers, fluoropolymers such as ETFE, PEEK, polyimides, and polyacetal can be preferably used. In addition, the outer tube main body 31 may be made of a plurality of materials, and a reinforcing member such as a wire rod may be embedded therein.

The cutting portion 40 is a cutter that cuts and removes an object such as a thrombus, a plaque, or a calcified lesion. Therefore, the "cut" means applying a force to such an object in contact to make the object smaller. A method for applying the force in the cutting and a shape or a form of the object after the cutting are not limited. The cutting portion 40 has enough strength to cut the above-described object. The cutting portion 40 is fixed to the distal portion of the drive shaft 20. The cutting portion 40 is a cylinder that protrudes toward the distal side with respect to the drive shaft 20. A sharp blade 41 is disposed at a distal end of the cutting portion 40. It is noted that a shape of the blade 41 is not particularly limited. The cutting portion 40 may include a large number of minute abrasive grains instead of the blade 41.

A constituent material for the cutting portion 40 preferably has sufficient strength to cut a thrombus, and for example, stainless steel, titanium, diamond, ceramics, a shape memory alloy such as a nickel-titanium alloy, a cemented carbide such as tungsten carbide, an alloy made of silver, copper, zinc, and the like (e.g., silver brazing filler metal), and high speed steel can be preferably used. The constituent material for the cutting portion 40 may be a resin such as engineering plastics such as polyether ether ketone (PEEK) and polyacetal.

Figure 3:
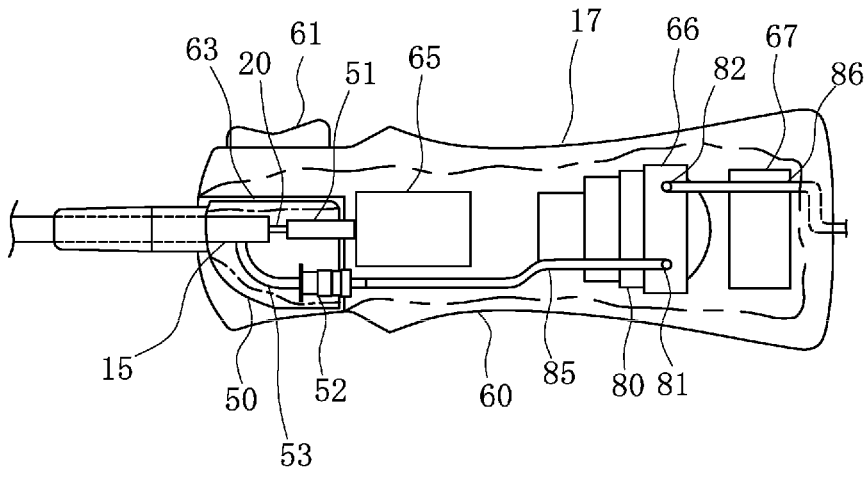
FIG. 3 is an enlarged front view showing an internal structure of a handle portion of a medical device.

The handle portion 17 will be described. As shown in FIG. 3, the handle portion 17 includes a housing 60, and an operation switch 61 for an operator to perform operation is provided on a distal side of the housing 60. A rotation driving source 65, which is a motor, a fluid driving source 66, which is a pump, and a power supply portion 67, which is a battery, are accommodated inside the housing 60. The rotation driving source 65 rotationally drives the drive shaft 20. The fluid driving source 66 moves a fluid from a distal side to a proximal side of the lumen 22. The power supply portion 67 is connected to the rotation driving source 65 and the fluid driving source 66, and supplies a power to them.

The housing 60 includes a hollow accommodation portion 63 on the distal side thereof. A connector 50 of the shaft portion 15 is provided at the proximal portion thereof and is accommodated in the accommodation portion 63. The connector 50 of the shaft portion 15 includes a rotation connection portion 51 and a fluid connection portion 52 therein. Therefore, positions of the rotation connection portion 51 and the fluid connection portion 52 are fixed.

The shaft portion 15 is branched inside the connector 50. The drive shaft 20 is interlocked with the rotation connection portion 51 of the shaft portion 15 whose central axis is coaxial with the drive shaft 20. The lumen 22 is drawn out toward a branch tube 53 side branched from the shaft portion 15, and the fluid connection portion 52 is provided at a distal portion of the branch tube 53.

Figure 4:
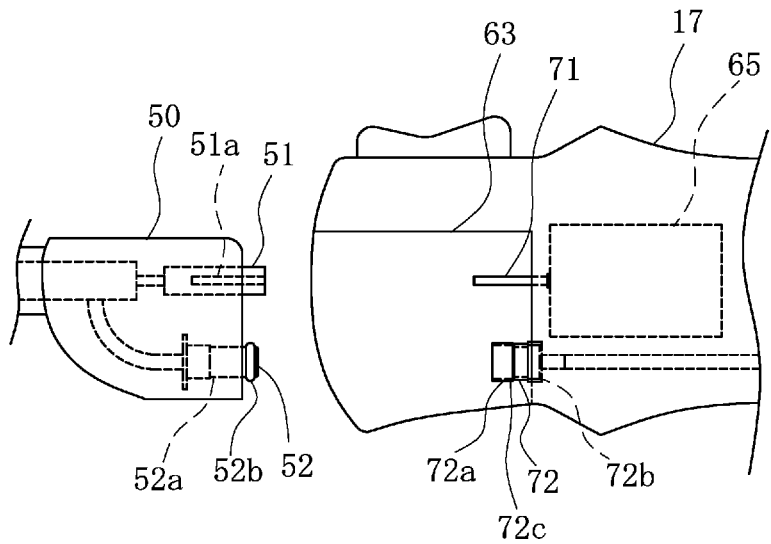
FIG. 4 is an exploded enlarged front view of a handle portion and a connection portion of a shaft portion.

As shown in FIG. 4, the rotation connection portion of the shaft portion 15 includes a shaft insertion portion 51a that is open to the proximal side. The rotation driving source 65 of the handle portion 17 includes a rotation connection portion 71 protruding into the accommodation portion 63. The rotation connection portion of the handle portion 17 is a rotation shaft of the rotation driving source 65. The rotation connection portion 71 of the handle portion 17 is fixed to the housing via the rotation driving source 65. The rotation connection portion 71 of the handle portion 17 is inserted into the shaft insertion portion 51a of the rotation connection portion 51 of the shaft portion 15, whereby the two are connected. The rotation connection portion 51 of the shaft portion 15 and the rotation connection portion of the handle portion 17 are fixed so as not to be movable relative to each other in a radial direction and a circumferential direction, but are not fixed in an axial direction. That is, these portions are connected in a state of not being locked to each other.

The fluid connection portion 52 of the shaft portion includes a cylindrical insertion portion 52*a*, and an O-ring 52*b* is attached to a distal portion thereof. The handle portion 17 includes a fluid connection portion 72 which is connected to the fluid connection portion 52 of the shaft portion 15. The fluid connection portion 72 of the handle portion 17 is fixed to the housing 60. The fluid connection portion 72 of the handle portion 17 includes a connector portion 72*a* that accommodates the insertion portion 52*a* of the fluid connection portion 52 of the shaft portion 15. The connector portion 72*a* includes a latch portion 72*b* that latches the fluid connection portion 52 of the shaft portion 15. An inner surface of the connector portion 72*a* has a slightly small diameter on a distal side of the latch portion 72*b*, and the O-ring 52*b* of the insertion portion 52*a* climbs over the small diameter portion and is elastically latched to the latch portion 72*b*. Accordingly, the fluid connection portion 52 of the shaft portion 15 is locked and connected to the fluid connection portion 72 of the handle portion 17.

A connection structure between the rotation connection portion 51 of the shaft portion 15 and the rotation connection portion 71 of the handle portion 17 is different from a connection structure between the fluid connection portion 52 of the shaft portion 15 and the fluid connection portion 72 of the handle portion 17. In addition, the rotation connection portion 51 of the shaft portion 15 and the rotation connection portion 71 of the handle portion 17 are connected in a state of not being locked to each other, and the fluid connection portion 52 of the shaft portion 15 and the fluid connection portion 72 of the handle portion 17 are locked and connected to each other. Therefore, when a lock on an aspiration side is released, connection on a rotation side is also easily released. Accordingly, even when aspiration cannot be performed during a procedure, rotation can be immediately stopped so as not to increase the number of the cut objects in the blood vessel.

The connector portion 72*a* is made of a resin material, and axial front and rear portions of the latch portion 72*b* are a deformable portion 72*c* that is elastically deformable in a radial direction. Therefore, when the operator presses, in the radial direction, the deformable portion 72*c* with a finger so as to deform the deformable portion 72*c*, the deformable portion 72*c* is elastically deformed, and a latch state of the insertion portion 52*a* with respect to the latch portion 72*b* is released accordingly. Therefore, the fluid connection portion 52 of the shaft portion 15 can be easily removed from the connector portion 72*a*. On the other hand, if the operator does not intentionally deform the deformable portion 72*c*, the latch state of the insertion portion 52*a* with respect to the latch portion 72*b* is maintained, and thus it is possible to prevent the fluid connection portion 52 of the shaft portion 15 from being unexpectedly detached from the fluid connection portion 72 of the handle portion 17.

Since the rotation connection portion 71 of the handle portion 17 and the fluid connection portion 72 of the handle portion 17 are both fixed to the housing 60 of the handle portion 17, positions of the rotation connection portion and the fluid connection portion 72 are fixed. As described above, the rotation connection portion 51 of the shaft portion 15 and the fluid connection portion 52 of the shaft portion 15 are also fixed. Therefore, by accommodating the connector 50 of the shaft portion 15 in the accommodation portion 63 of the handle portion 17, the rotation connection portion 51 of the shaft portion 15 can be connected to the rotation connection portion 71 of the handle portion 17, and the fluid connection portion 52 of the shaft portion 15 can be connected to the fluid connection portion 72 of the handle portion 17.

Figure 5:
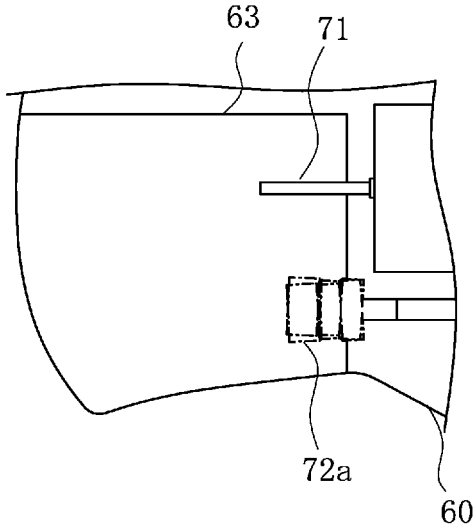
FIG. 5 is an enlarged front view showing an accommodation portion of a handle portion.

As shown in FIG. 5, the connector portion 72*a* can be slightly deformed such that the axial direction of the connector portion 72*a* is tilted with respect to the housing 60. On the other hand, in order to rotationally drive the drive shaft 20, the rotation connection portion 71 of the handle portion provided on the rotation driving source 65 is fixed so as not to tilt the axial direction thereof. Therefore, the drive shaft 20 can be stably rotationally driven, and even if a dimensional error occurs in a positional relationship between the rotation connection portion 51 of the shaft portion and the fluid connection portion 52 of the shaft portion, these connection portions can be reliably connected to the handle portion 17.

In the handle portion 17, the rotation driving source 65, the fluid driving source 66, and the power supply portion 67 are disposed in this order from the distal side toward the proximal side. These portions are disposed such that central axes thereof are substantially coaxial. Accordingly, gravity center positions of the rotation driving source 65, the fluid driving source 66, and the power supply portion 67 can be arranged substantially in a straight line along a longitudinal direction of the handle portion 17, so that the operator can easily operate the shaft portion 15 while holding the handle portion 17.

A pump main body 80 of the fluid driving source 66 has an injection port 81 as an inlet and a discharge port 82 as an outlet. An injection tube 85 extending from the fluid connection portion 72 of the handle portion 17 is connected to the injection port 81. A discharge tube 86 is connected to the discharge port 82. The discharge tube 86 is drawn out to an outside of the housing 60. A part or all of a portion of the discharge tube 86 drawn out to the outside of the housing 60 is transparent or translucent. Accordingly, the operator can visually recognize an inside of the discharge tube 86. It is noted that a portion of the discharge tube 86 disposed inside the housing 60 may or may not be transparent or translucent. The discharge tube 86 is connected to an aspiration bag (not shown) outside the handle portion 17.

Figure 6:
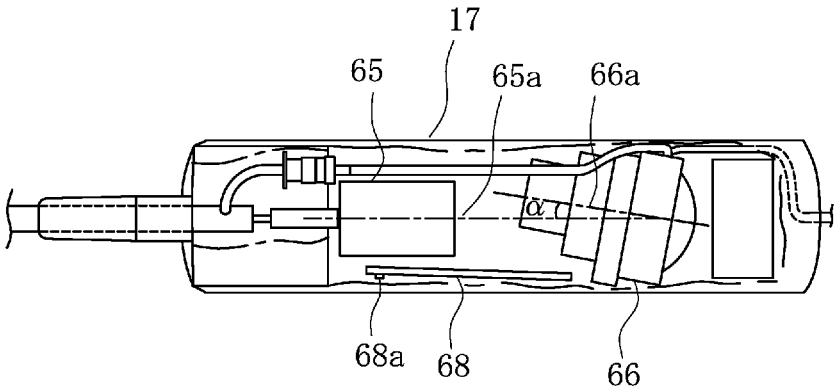
FIG. 6 is an enlarged bottom view showing an internal structure of a handle portion.

As shown in FIG. 6, a central axis 66*a* of the fluid driving source 66 is tilted at an angle α with respect to a rotation axis 65*a* of the rotation driving source 65. Accordingly, a length of the fluid driving source 66 in the longitudinal direction connecting a proximal end and a distal end of the handle portion 17 can be reduced, and the handle portion 17 can be shortened, so that the operator can easily operate the handle portion 17.

Figure 7A:
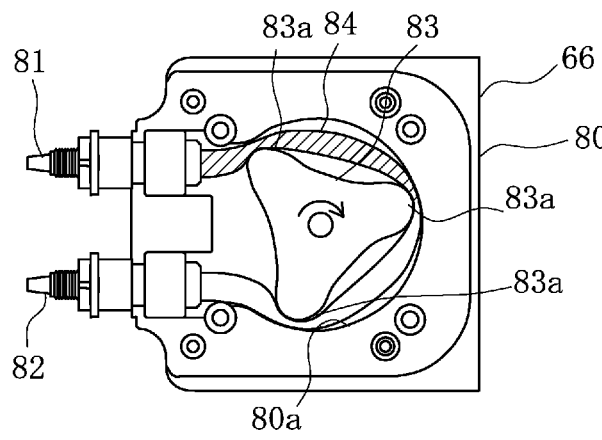
FIGS. 7A-7C are front views each illustrating an internal structure of a fluid driving source.

As shown in FIG. 7A, the fluid driving source 66 includes a driving portion 83 and an inner tube 84 inside the pump main body 80 having the injection port 81 and the discharge port 82. The pump main body 80 includes a wall portion 80*a* therein, and the inner tube 80 is disposed along the wall portion 80*a*. The driving portion 83 is driven by a motor and rotatable at a center portion, and includes, in a circumferential direction, a plurality of pressing portions 83*a* protruding in a radial direction from the center portion.

Figure 7B:
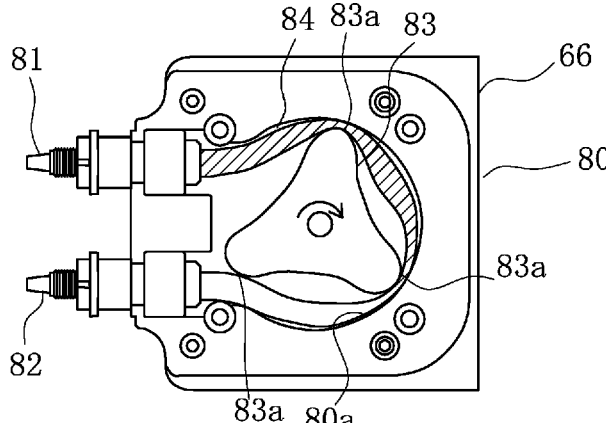
Figure 7C:
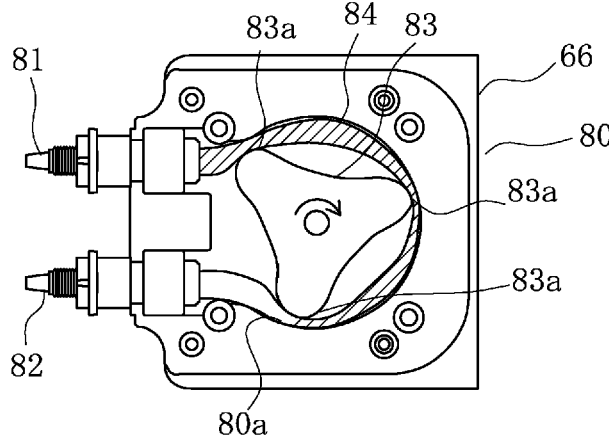

The inner tube 84 communicates with the lumen 22, and is disposed over approximately 270° so as to surround the driving portion 83. An outer peripheral portion of each pressing portion 83*a* of the driving portion 83 is in pressure contact with the inner tube 84. The pressing portions 83*a* move in the circumferential direction while deforming the inner tube 84 at a plurality of positions between the pressing portions 83*a* and the wall portion 80*a*. A portion of the inner tube 84 is pressed by the pressing portions 83a of the driving portion 83, but an inner flow path is not completely closed, and a communicating region remains. As shown in FIG. 7B and FIG. 7C, the fluid in the inner tube 84 indicated by hatching in the drawings moves toward the discharge port 82 side in accordance with the rotation of the driving portion 83. Accordingly, the fluid inside the inner tube 84 is conveyed in a certain direction from the injection port 81 toward the discharge port 82.

In this way, by using a pump that acts from an outer surface of the inner tube 84 to convey the fluid inside the inner tube 84 as the fluid driving source 66, even if the fluid aspirated into the shaft portion 15 or the inner tube 84 contains a hard calcareous fragment, a plaque, and the like, the objects do not come into direct contact with the driving portion 83, and therefore, it is possible to prevent an operation from being stopped due to the fragment, the plaque, and the like being caught in the driving portion 83. Accordingly, even when the fluid containing the object cut by the cutting portion 40 is aspirated by the fluid driving source 66, the fluid driving source 66 can be prevented from being stopped. The inner tube 84 of the fluid driving source 66 is made of a material capable of EO sterilization or a material capable of electron beam sterilization. Examples of such a material include a pharmed BPT and a silicon tube. However, the inner tube 84 may be formed of a material other than these materials. As for bending strength related to difficulty of kinking a tube or resistance of an inner diameter to be crushed, it is desirable that the injection tube 85 is larger than the inner tube 84 and the discharge tube 86 is larger than the injection tube 85. The injection tube 85 and the discharge tube 86 are made of a material which is thicker than the inner tube 84 and is hardly broken. In addition, a blade may be wound around a tube body of the injection tube 85 and the discharge tube 86. Since a negative pressure is applied to an inside of the injection tube 85, a kink occurs and the aspiration cannot be performed, and thus high bending strength is required. In the discharge tube 86, when the kink occurs, the aspirated object cannot reach a collection bag, and the discharge tube 86 may be damaged due to an increase in an internal pressure, and thus higher bending strength is required. Since the inner tube 84 is a tube having small bending strength and a small thickness, the inner tube 84 is easily deformed by the driving portion 83, and the fluid inside the inner tube 84 can be easily moved. However, the inner tube 84, the injection tube 85, and the discharge tube 86 may have the same bending strength. In addition, a diameter and the material for the inner tube 84 can be changed according to other components such as the driving portion 83 and the fluid driving source 66 to be used.

When the fluid driving source 66 in which the inner tube 84 is disposed so as to surround a periphery of the driving portion 83 by 180° is used, the injection port 81 and the discharge port 82 can be disposed on both sides of the pump main body 80. In such a case, as shown in FIG. 8, an angle α between the central axis 66a of the fluid driving source 66 and a direction of the rotation axis 65a of the rotation driving source 65 can be set to 90°. The injection tube 85 and the discharge tube 86 which are connected to the fluid driving source 66 are arranged substantially in a straight line inside the handle portion 17. Accordingly, space efficiency inside the handle portion 17 can be further improved, and the handle portion 17 can be miniaturized. In addition, since the injection tube 85 protrudes from a side surface of the fluid driving source 66, the injection tube 85 is disposed at a position away from a central axis of the housing 60. Similarly, since the fluid connection portion 52 of the shaft portion 15 is located at a position away from the central axis of the housing 60, the injection tube 85 and the fluid connection portion 52 of the shaft portion 15 are arranged substantially in a straight line. Accordingly, the fluid driving source 66 can easily aspirate the fluid. In addition, the injection tube 85 is arranged in parallel in the vicinity of the rotation driving source 65. Accordingly, blood or the like moving in the injection tube 85 and the injection tube 85 can cool the rotation driving source 65. In addition, the fluid driving source 66, which is larger than the rotation driving source 65, is located on a proximal side of the rotation driving source 65. Accordingly, a circumferential length of an outer surface of the housing 60 can be shortened from the proximal side toward the distal side, and the housing 60 can be formed into a shape that can be easily gripped by the operator. Examples of the fluid driving source 66 include an aspiration pump, a screw pump, and a peristaltic pump that generate a negative pressure from an outside.

As shown in FIG. 6, a control board 68 is further disposed inside the handle portion 17. The control board 68 is connected to the power supply portion 67, and includes a control circuit (not shown) that controls the rotation driving source 65 and the fluid driving source 66 based on the operation of the operation switch 61. The control board 68 is disposed so as to extend from a side portion of the rotation driving source 65 to a side portion of the fluid driving source 66, and is slightly inclined with respect to the longitudinal direction of the handle portion 17. Accordingly, the space efficiency of the control board 68 inside the handle portion 17 is improved. In addition, the control board 68 includes a light emitting portion 68a at a position on a distal side thereof. The light emitting portion 68a indicates operation states of the rotation driving source 65 and the fluid driving source 66 or an alert or the like as necessary. By disposing the light emitting portion 68a at this position, the light emitting portion 68a is disposed in a gap between an index finger and a thumb when the operator holds the handle portion 17 with a hand, and thus the operator can easily visually recognize the light emitting portion 68a.

In the above example, the rotation driving source 65 and the fluid driving source 66 are connected to the control board 68 and driven by the single power supply portion 67, but the rotation driving source 65 and the fluid driving source 66 may be controlled by independent circuits and include the respective power supply portions 67. Accordingly, it is possible to prevent one from being affected by a current or voltage change due to an operation of the other. In addition, the control board 68 is located at a side opposite the injection tube 85. Accordingly, a space is secured around the injection tube 85, and the injection tube 85 can be disposed substantially in a straight line.

FIGS. 9A and 9B show a modified handle portion 18. As shown in FIGS. 9A and 9B, the rotation driving source and the fluid driving source 66 may be arranged in parallel along a direction orthogonal to a longitudinal direction connecting a distal end and a proximal end of the handle portion 18. Accordingly, a length of the handle portion 18 can be shortened. When the length of the handle portion 18 is short, usability of the handle portion 18 is improved, and the operator can more easily operate the handle portion 18.

In addition, the power supply portion 67 may be disposed radially outside the rotation driving source 65 and the fluid driving source 66 inside the handle portion 18. Accordingly, the rotation driving source 65, the fluid driving source 66, and the power supply portion 67, which are heavy, are all located in the hand of the operator, so that a gravity center position of the handle portion 18 is positioned at a center of the hand that grips the handle portion 18, and the handlability can be further improved.

With respect to a positional relationship between the rotation connection portion 51 of the shaft portion 15 and the fluid connection portion 52 of the shaft portion 15 in a direction of inserting into the handle portion 17 (or 18), it is desirable that the rotation connection portion 51 of the shaft portion 15 is not connected to the rotation connection portion 71 of the handle portion 17 in a state where the fluid connection portion 52 of the shaft portion is not correctly connected to the fluid connection portion 72 of the handle portion 17. With such a positional relationship, it is possible to prevent the drive shaft 20 from starting to rotate without starting to aspirate the fluid.

Figure 10:
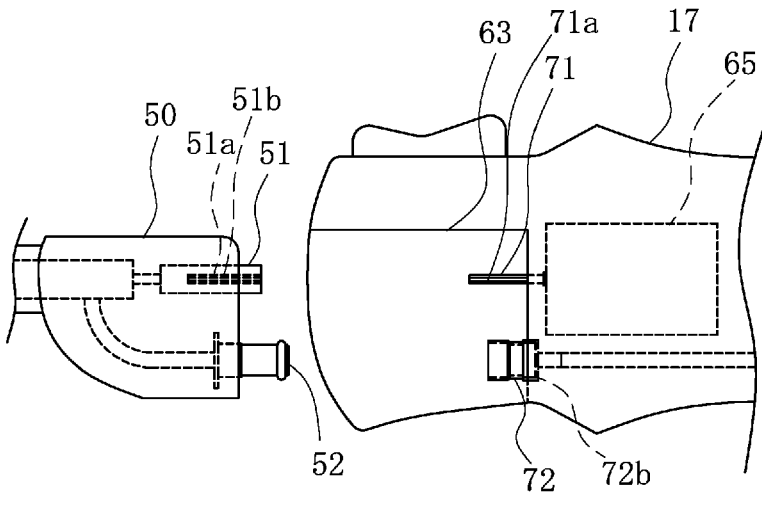
FIG. 10 is an exploded enlarged front view showing a handle portion and a connection portion of a shaft portion.

As a positional relationship for this, as shown in FIG. 10, the rotation connection portion 51 of the shaft portion 15 can be disposed such that a proximal position thereof is located on the distal side or at the same position as a proximal position of the fluid connection portion 52 of the shaft portion 15. In the shaft insertion portion 51a of the rotation connection portion 51 of the shaft portion 15, a shaft insertion portion 51a including a fitting gear portion 51b formed on an inner surface thereof is fitted to a gear portion 71a formed on a surface of the rotation connection portion 71 on the handle portion side. According to the positional relationship in FIG. 10, the fitting gear portion 51b can be prevented from being fitted to the gear portion 71a of the rotation connection portion 71 of the handle portion 17 until the fluid connection portion 52 of the shaft portion is connected to and locked by the fluid connection portion 72 of the handle portion, and the rotation connection portion can be prevented from being rotatably connected unless the fluid connection portions are connected.

Figure 11:
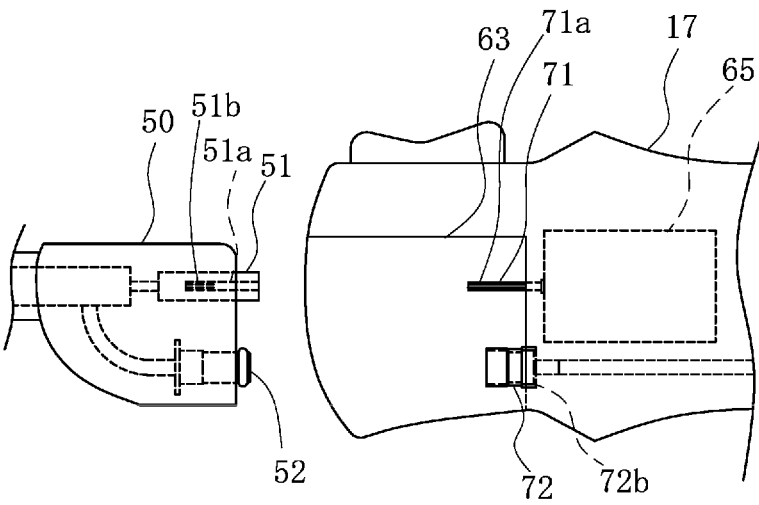
FIG. 11 is an exploded enlarged front view showing a handle portion and a connection portion of a shaft portion.

In addition, as shown in FIG. 11, when the proximal position of the rotation connection portion 51 of the shaft portion 15 is located on the proximal side with respect to the proximal position of the fluid connection portion 52 of the shaft portion 15, the fitting gear portion 51b formed on the inner surface of the shaft insertion portion 51a may be formed only on a distal side of the shaft insertion portion 51a without being formed on a proximal side of the shaft insertion portion 51a. Since the gear portion 71a of the rotation connection portion 71 of the handle portion can be inserted into the proximal side of the shaft insertion portion 51a but is not fitted thereto, the fitting gear portion 51b can be prevented from being fitted to the gear portion 71a of the rotation connection portion 71 of the handle portion 17 until the fluid connection portion 52 of the shaft portion 15 is connected to and locked by the fluid connection portion 72 of the handle portion 17. Accordingly, the rotation connection portion can be prevented from being rotatably connected unless the fluid connection portions are connected.

In a positional relationship of FIG. 11, the gear portion 71a formed in the rotation connection portion 71 of the handle portion 17 may be formed only on a distal side of the rotation connection portion 71 of the handle portion 17. In addition, when the fitting gear portion 51b is formed on the entire rotation connection portion 51 of the shaft portion 15, the gear portion 71a may be formed only on a proximal side of the rotation connection portion 71 of the handle portion 17.

In addition, although the rotation connection portion of the shaft portion 15 and the rotation connection portion 71 of the handle portion 17 are fixed to each other by a gear structure, magnets may be provided on both of the connection portions so that the connection portions are easily connected to each other.

As described above, the medical device 10 includes: the long shaft portion 15 that includes the drive shaft 20 and the lumen 22; the cutting portion 40 that is disposed at a distal portion of the shaft portion 15 and cuts an object; the handle portion 17 that accommodates the rotation driving source 65 that rotates the drive shaft 20; and the fluid driving source 66 that moves the fluid from the distal side to the proximal side of the lumen 22, in which the fluid driving source 66 is accommodated in the handle portion 17, the rotation connection portion 71 of the handle portion 17 connected to the rotation connection portion 51 of the shaft portion 15 and the fluid connection portion 72 of the handle portion 17 connected to the fluid connection portion 52 of the shaft portion 15 are provided in the handle portion 17, and the rotation connection portion 51 of the shaft portion 15 that connects the drive shaft 20 to the rotation driving source 65 and the fluid connection portion 52 of the shaft portion 15 that connects the lumen 22 to the fluid driving source 66 are provided at the proximal portion of the shaft portion 15. In the medical device 10 configured as described above, since the rotation connection portion 51 of the shaft portion 15 and the fluid connection portion 52 of the shaft portion 15 can be integrally attached to the handle portion 17, the lumen 22 is reliably connected to the fluid driving source 66.

In addition, the positions of the rotation connection portion 51 of the shaft portion 15 and the fluid connection portion 52 of the shaft portion 15 are fixed. Accordingly, the rotation connection portion 51 of the shaft portion 15 and the fluid connection portion 52 of the shaft portion 15 can be connected at once.

In addition, the shaft portion 15 is attachable to and detachable from the handle portion 17. Accordingly, the handle portion 17 can be repeatedly used.

In addition, the rotation connection portion 71 of the handle portion 17 and the fluid connection portion 72 of the handle portion 17 may be provided in the handle portion 17. Accordingly, the connector 50 of the shaft portion 15 can be easily attached to the handle portion 17.

In addition, the rotation connection portion 51 of the shaft portion 15 and the fluid connection portion 52 of the shaft portion 15 are arranged substantially parallel to each other. Accordingly, by inserting the connector 50 of the shaft portion 15 in parallel to the handle portion 17, the rotation connection portion 51 of the shaft portion 15 and the fluid connection portion 52 of the shaft portion 15 can be easily connected to each other.

In addition, the rotation connection portion 71 of the handle portion 17 and the fluid connection portion 72 of the handle portion 17 are arranged substantially parallel to each other. Accordingly, the rotation connection portion 51 of the shaft portion 15 and the fluid connection portion 52 of the shaft portion 15 can be easily connected to the rotation connection portion 71 of the handle portion 17 and the fluid connection portion 72 of the handle portion 17, respectively.

In addition, the rotation connection portion 51 of the shaft portion 15 and the fluid connection portion 52 of the shaft portion 15 are disposed to have an angle with respect to respective axes (see FIG. 9B). In other words, the axis of the fluid connection portion 52 is inclined with respect to the rotation axis of the rotation connection portion 51. With this configuration, the connector 50 including the inclined fluid connection portion 52 can be formed to fit with the outer shape of the handle portion 18.

In addition, either a first connection between the rotation connection portion 51 of the shaft portion 15 and the rotation connection portion 71 of the handle portion or a second connection between the fluid connection portion 52 of the shaft portion 15 and the fluid connection portion 72 of the handle portion 17 can be locked. Accordingly, for example, when the aspiration in the lumen 22 is not performed, the connector 50 of the shaft portion 15 can be easily removed from the handle portion 17, and the rotation of the drive shaft 20 can be immediately stopped.

In addition, the locked connection of either the first connection or the second connection is lockable and unlockable. Accordingly, the lock can be attached and detached for either connection.

In addition, the rotation connection portion 51 of the shaft portion 15 may not be fixed to the rotation connection portion 71 of the handle portion 17 in the axial direction, and the fluid connection portion 52 of the shaft portion 15 may be fixed to the fluid connection portion 72 of the handle portion 17 in the axial direction. Accordingly, the rotation of the drive shaft 20 can be immediately stopped only by removing the fluid connection portion 52 of the shaft portion 15 from the fluid connection portion 72 of the handle portion 17.

In addition, the fluid connection portion 72 of the handle portion 17 may include the connector portion 72a that accommodates the fluid connection portion 52 of the shaft portion 15, and the connector portion 72a may include the latch portion 72b that latches the fluid connection portion 52 of the shaft portion 15, and may include, on the axial front and rear portions of the latch portion 72b, the deformable portion 72c that is elastically deformable. Accordingly, the connector portion 72a can reliably hold the fluid connection portion 52 of the shaft portion 15, while the fluid connection portion 52 of the shaft portion can be easily removed by elastically deforming the deformable portion 72c.

In addition, the connector portion 72a may be deformable such that the axial direction of the connector portion 72a is tilted with respect to the handle portion 17. Accordingly, while the rotation axis of the rotation driving source 65 is fixed, a dimensional error of the fluid connection portion 52 of the shaft portion 15 can be absorbed, and the connector 50 of the shaft portion 15 can be easily attached.

In addition, the fluid connection portion 52 of the shaft portion 15 may be connected to the branch tube 53 branched from the shaft portion 15, and the branch tube 53 may be bent. Accordingly, the rotation connection portion 51 of the shaft portion 15 and the fluid connection portion 52 of the shaft portion 15 can be arranged in parallel.

In addition, the positions of the rotation connection portion 71 of the handle portion 17 and the fluid connection portion 72 of the handle portion 17 may be fixed. Accordingly, the connector 50 of the shaft portion 15 can be easily attached.

It is noted that the present invention is not limited to the embodiments described above, and various modifications can be made by those skilled in the art within a scope of the technical idea of the present invention. In the above-described embodiments, the connection structure between the rotation connection portion 51 of the shaft portion 15 and the rotation connection portion 71 of the handle portion 17 is different from the connection structure between the fluid connection portion 52 of the shaft portion 15 and the fluid connection portion 72 of the handle portion 17, but those connection structures may be the same. In addition, the rotation connection portion 51 of the shaft portion 15 and the rotation connection portion 71 of the handle portion 17 are not locked, and the fluid connection portion 52 of the shaft portion 15 and the fluid connection portion 72 of the handle portion 17 are locked, but both the connection structures may be a locked structure.

In addition, both the connection structure between the rotation connection portion 51 of the shaft portion 15 and the rotation connection portion 71 of the handle portion and the connection structure between the fluid connection portion 52 of the shaft portion 15 and the fluid connection portion 72 of the handle portion 17 may not be a locked structure. In such a case, a latch portion or the like for locking is provided on the connector 50 of the shaft portion 15 and the housing 60.

In addition, the rotation connection portion 71 of the handle portion 17 and the fluid connection portion 72 of the handle portion 17 may be coaxially arranged. In such a case, the rotation connection portion 71 of the handle portion 17 is formed in a hollow shape, and the fluid connection portion 72 of the handle portion 17 is disposed inside the hollow of the rotation connection portion 71 of the handle portion 17. In addition, the rotation connection portion 51 of the shaft portion 15 and the fluid connection portion 52 of the shaft portion 15 are also coaxially arranged and connected to the rotation connection portion 71 of the handle portion 17 and the fluid connection portion 72 of the handle portion 17, respectively.

In addition, in the above-described embodiments, the rotation connection portion 51 of the shaft portion 15 and the fluid connection portion 72 of the shaft portion 17 are arranged substantially parallel to each other, but may be disposed to have an angle with respect to the respective axes.

In addition, the fluid driving source 66 may be provided outside the handle portion 17. In addition, the power supply portion 67 may also be provided outside the handle portion 17, or a power may be supplied from an outside. In addition, the type of the fluid driving source is not limited to a pump that generates a negative pressure from the outside, and may be a pump such as a diaphragm pump in which a driving portion is in direct contact with a fluid.

In addition, the rotation connection portion 71 of the handle portion 17 and the fluid connection portion 72 of the handle portion 17 may not be fixed in the handle portion 17. In such a case, the rotation connection portion 71 of the handle portion 17 and the fluid connection portion 72 of the handle portion 17 are fixed in a member separate from the handle portion 17, and the rotation connection portion 71 and the fluid connection portion 72 are connected to the handle portion 17 by a rotation shaft or a tube.

Figure 12:
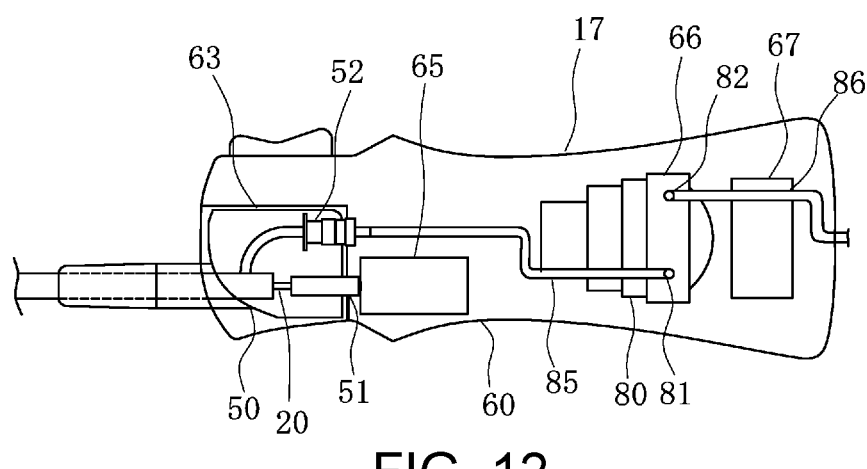
FIG. 12 is an enlarged bottom view showing an internal structure of a handle portion.

In addition, as shown in FIG. 12, the rotation driving source 65 may be disposed such that the central axis thereof is disposed at a position away from the central axis of the fluid driving source 66. Accordingly, a terminal of the rotation driving source 65 is separated from the fluid driving source 66, and electromagnetic noise can be reduced.

Figure 13A:
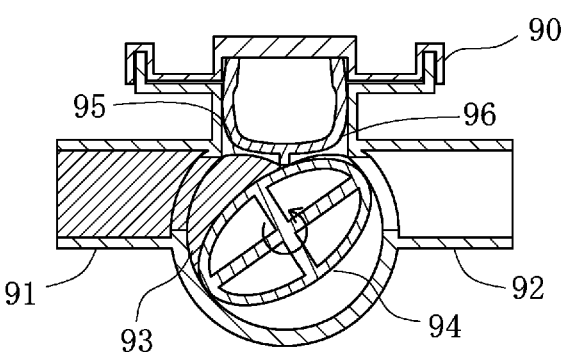
FIGS. 13A-13C are cross-sectional views each illustrating an internal structure of a fluid driving source.
Figure 13B:
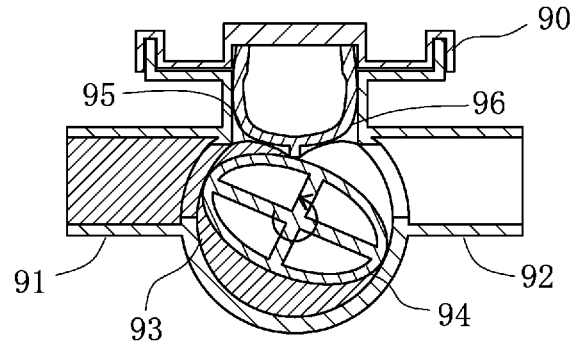
Figure 13C:
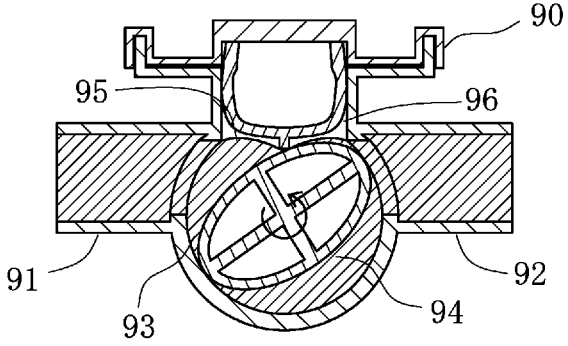

In addition, a pump shown in FIGS. 13A-13C may be used as a fluid driving source. As shown in FIG. 13A, a fluid driving source 90 includes an aspiration port 91 communicating with the lumen 22, a flow path portion 93 communicating with the aspiration port 91, and a discharge port 92 communicating with the flow path portion 93. The flow path portion 93 is provided with a driving portion 94 having an elliptical cross section. A seal member 95 biased by an elastic pressing body 96 is in contact with the driving portion 94. The seal member 95 constantly connects a surface of the driving portion 94 by the biasing of the elastic pressing body 96 when the driving portion 94 is rotated. In FIGS. 13A-13C, the fluid is indicated by hatching.

As shown in FIG. 13B, when the driving portion 94 is rotated, the fluid from the injection port 92 enters along a circumferential direction of the flow path portion 93. As shown in FIG. 13C, when the driving portion 94 is further rotated, the fluid is pushed out from the flow path portion 93 to the discharge port 92. Since an upper portion of the driving portion 94 is sealed with the seal member 95, the fluid is conveyed in one direction from the injection port 92 toward the discharge port 92 by the driving portion 94. In this way, by using the pump in which the fluid is conveyed in one direction by the driving portion 94 as the fluid driving source 90, even if the fluid aspirated into the shaft portion 15 or the inner tube 84 contains the hard calcareous fragment, the plaque, and the like, the objects are conveyed by a mechanical pressing force of the driving portion 94 compared to a pump that generates a negative pressure to perform aspiration, and thus clogging inside the fluid driving source 90 can be prevented. It is noted that the aspiration means that the fluid is drawn from an outside to an inside of the shaft portion or the inner tube and the fluid is moved in the shaft portion or the inner tube. In addition, the conveyance means that the fluid is moved in the shaft portion or the inner tube by the mechanical pressing force.

What is claimed is:

1. A medical device for removing an object in a body cavity, comprising:
   a rotatable drive shaft having a lumen;
   a cutter disposed at a distal portion of the drive shaft and by which the object is cut;
   a first rotation connection portion at a proximal portion of the drive shaft and by which a rotational force is transmitted to the drive shaft;
   a first fluid connection portion at the proximal portion of the drive shaft and through which the object that has been moved with a fluid through the lumen is removed; and
   a handle including:
      a second rotation connection portion, a distal end of which is connectable to a proximal end of the first rotation connection portion in a first direction parallel to a rotation axis of the drive shaft,
      a second fluid connection portion, a distal end of which is connectable to a proximal end of the first fluid connection portion in the first direction,
      a rotation driving source connected to the second rotation connection portion and configured to generate the rotational force, and
      a fluid driving source configured to move the fluid from the distal portion to the proximal portion of the drive shaft via the first and second fluid connection portions.

2. The medical device according to claim 1, further comprising:
   a connector that houses the first rotation connection portion and the first fluid connection portion, wherein a proximal end of the connector is connectable to a distal end of the handle.

3. The medical device according to claim 2, wherein the connector is detachable from the handle in the first direction.

4. The medical device according to claim 1, wherein the first and second rotation connection portions extend along the same direction when connected.

5. The medical device according to claim 1, wherein the first and second fluid connection portions extend along the same direction when connected.

6. The medical device according to claim 1, wherein a part of the first fluid connection portion extends along a second direction that is inclined with respect to a rotation axis of the first rotation connection portion.

7. The medical device according to claim 1, wherein the first rotation connection portion is lockable to the second rotation connection portion.

8. The medical device according to claim 7, wherein the first fluid connection portion is lockable to the second fluid connection portion.

9. The medical device according to claim 1, wherein the first fluid connection portion is lockable to the second fluid connection portion.

10. The medical device according to claim 1, wherein the first rotation connection portion has an insertion portion into which the second rotation connection portion can be inserted.

11. The medical device according to claim 1, wherein the second fluid connection portion includes a connector portion into which the first fluid connection portion can be inserted.

12. The medical device according to claim 11, wherein the connector portion includes:
   a latch portion that latches the first fluid connection portion, and
   a deformable portion that is elastically deformable on each side of the latch portion in the axial direction.

13. The medical device according to claim 12, wherein the deformable portion is deformable such that an axis of the connector portion can be tilted with respect to the handle.

14. The medical device according to claim 1, further comprising:
   a branch tube branched from the drive shaft to the first fluid connection portion.

15. The medical device according to claim 14, wherein the branch tube is bent.

16. The medical device according to claim 1, wherein the second rotation connection portion is rotatably fixed to the handle, and the second fluid connection portion is fixed to the handle.

17. A medical device for removing an object in a body cavity, comprising:
   a shaft portion including:
      a rotatable drive shaft having a first lumen,
      a cutter disposed at a distal portion of the drive shaft and by which the object is cut, and
      a connector disposed at a proximal portion of the drive shaft, including a second lumen that communicates with the first lumen, and by which a rotational force is transmitted to the drive shaft, the cut object being removed with a fluid through the second lumen; and
   a handle portion, a distal end of which is connectable to a proximal end of the connector in a first direction parallel to a rotation axis of the drive shaft, the handle portion including:
      a first motor configured to generate the rotational force, and
      a fluid driving source configured to move the fluid from the distal portion to the proximal portion of the drive shaft when the distal end of the handle portion is connected to the proximal end of the connector.

18. The medical device according to claim 17, wherein the connector is detachable from the handle portion.

19. The medical device according to claim 17, wherein the fluid driving source includes:
   a fluid flow path having an inlet and an outlet, the inlet communicating with the first and second lumens when the connector is connected to the handle portion,
   a rotatable portion in the fluid flow path, and a second motor configured to rotate the rotatable portion such that the fluid that has flowed into the fluid flow path from the inlet moves toward the outlet.

20. The medical device according to claim 17, wherein the fluid driving source is a pump.

* * * * *